(12) United States Patent
Toyoshima et al.

(10) Patent No.: US 7,569,264 B2
(45) Date of Patent: Aug. 4, 2009

(54) TOPSHEET FOR ABSORBENT ARTICLE

(75) Inventors: Yasuo Toyoshima, Tochigi (JP); Hiroko Sugiura, Tochigi (JP); Noriko Sakamoto, Tochigi (JP); Taiki Uchiyama, Tochigi (JP); Koji Asano, Tochigi (JP)

(73) Assignee: Kao Corporation, Tokyo (JP)

( * ) Notice: Subject to any disclaimer, the term of this patent is extended or adjusted under 35 U.S.C. 154(b) by 280 days.

(21) Appl. No.: 10/327,983

(22) Filed: Dec. 26, 2002

(65) Prior Publication Data

US 2003/0143376 A1    Jul. 31, 2003

(30) Foreign Application Priority Data

Dec. 28, 2001 (JP) ............................. 2001-398779
Oct. 16, 2002 (JP) ............................. 2002-301297

(51) Int. Cl.
   *B32B 3/00*       (2006.01)
   *B32B 5/14*       (2006.01)
   *B32B 27/14*      (2006.01)

(52) U.S. Cl. ...................... 428/156; 428/170; 428/196; 428/198

(58) Field of Classification Search ................. 428/156, 428/170, 171, 172, 196, 198; 442/381
See application file for complete search history.

(56) References Cited

U.S. PATENT DOCUMENTS 4,041,203 A    8/1977    Brock et al.
4,323,068 A *  4/1982    Aziz ........................... 604/378
4,551,378 A   11/1985    Carey, Jr.

(Continued)

FOREIGN PATENT DOCUMENTS

CN    1178101 A    4/1998

(Continued)

OTHER PUBLICATIONS

English language abstract of Japanese patent document 06017361 (Jan. 25, 1994).

(Continued)

*Primary Examiner*—Norca L Torres-Velazquez
(74) *Attorney, Agent, or Firm*—Birch, Stewart, Kolasch & Birch, LLP

(57) ABSTRACT

A topsheet for absorbent articles having absorbing performance for smoothly transferring liquid body waste, e.g., menstrual blood or urine, to an underlying absorbent member and surface characteristics such that the surface thereof in contact with wearer's skin is soft enough not to cause skin irritation. The topsheet 1 comprises a first layer 11 disposed on the side of a wearer and a second layer 12 disposed on the side of an absorbent member, the first layer and the second layer being partly joined together, and having protrusions and depressions on the side of a wearer, wherein the first and second layers each comprise a fiber aggregate, the first layer has fusion-bonded fiber intersections, the first layer has an apparent thickness (t1) of 0.1 to 5 mm, the second layer has an apparent thickness (t2) of 0.2 to 3 mm, the apparent thickness ratio of the first layer to the second layer (t1/t2) is 0.5 to 8, the first layer has a fiber density (d1) of 0.001 to 0.05 g/cm³, the second layer has a fiber density (d2) of 0.03 to 0.2 g/cm³, and the fiber density (d2) of the second layer is higher than that (d1) of the first layer.

7 Claims, 3 Drawing Sheets

U.S. PATENT DOCUMENTS

| | | | |
|---|---|---|---|
| 4,720,415 A | | 1/1988 | Vander Wielen et al. |
| 4,935,022 A | * | 6/1990 | Lash et al. .................. 604/368 |
| 5,143,779 A | * | 9/1992 | Newkirk et al. ............. 428/218 |
| 5,229,191 A | | 7/1993 | Austin |
| 5,348,547 A | * | 9/1994 | Payne et al. .................. 604/378 |
| 5,399,174 A | | 3/1995 | Yeo et al. |
| 5,491,016 A | | 2/1996 | Kaiser et al. |
| 5,536,555 A | | 7/1996 | Zelazoski et al. |
| 5,591,149 A | * | 1/1997 | Cree et al. .................. 604/368 |
| 5,612,118 A | | 3/1997 | Schleinz et al. |
| 5,817,394 A | | 10/1998 | Alikhan et al. |
| 5,989,688 A | * | 11/1999 | Barge et al. .................. 442/381 |
| 6,362,391 B1 | | 3/2002 | Mizutani et al. |
| 6,673,418 B1 | * | 1/2004 | DeOlivera et al. .......... 428/172 |
| 2002/0068150 A1 | | 6/2002 | Taneichi et al. |
| 2003/0134094 A1 | | 7/2003 | Zafiroglu et al. |
| 2003/0162460 A1 | | 8/2003 | Saka et al. |

FOREIGN PATENT DOCUMENTS

| | | |
|---|---|---|
| EP | 0327317 A2 | 8/1989 |
| EP | 359501 A2 * | 3/1990 |
| EP | 0604731 A1 | 7/1994 |
| EP | 0841156 A1 | 5/1998 |
| EP | 1338262 A1 | 8/2003 |
| GB | 2288412 A | 10/1995 |
| JP | 51-146584 A | 12/1976 |
| JP | 61-124667 A | 6/1986 |
| JP | 62-141167 A | 6/1987 |
| JP | 63-296936 A | 12/1988 |
| JP | 63-309657 A | 12/1988 |
| JP | 2-133641 A | 5/1990 |
| JP | 02-300365 A | 12/1990 |
| JP | 04-312431 A | 11/1992 |
| JP | 5-25763 A | 2/1993 |
| JP | 6017356 A | 1/1994 |
| JP | 6-128853 A | 5/1994 |
| JP | 7-232409 A | 9/1995 |
| JP | 8-3850 A | 1/1996 |
| JP | 9-003755 A | 1/1997 |
| JP | 9-111631 A | 4/1997 |
| JP | 09-117982 A | 5/1997 |
| JP | 10-80445 A | 3/1998 |
| JP | 2000-135239 A | 5/2000 |
| JP | 2000-210334 A | 8/2000 |
| JP | 3131557 B2 | 11/2000 |
| JP | 2001-37805 A | 2/2001 |
| JP | 3181195 B2 | 4/2001 |
| JP | 3181195 B2 | 4/2001 |
| JP | 2001-140158 A | 5/2001 |
| WO | WO-98/24389 A1 | 6/1998 |
| WO | WO-00/35503 A1 | 6/2000 |

OTHER PUBLICATIONS

English language abstract of Japanese patent document 09003755 (Jan. 7, 1997).

English language abstract of Japanese patent document 09111631 (Apr. 28, 1997).

* cited by examiner

TOPSHEET FOR ABSORBENT ARTICLE

FIELD OF THE INVENTION

The present invention relates to absorbent articles, such as sanitary napkins, panty liners, incontinence pads, and disposable diapers, and a sheet which is used in the absorbent articles as a topsheet to be brought into contact with a wearer's body.

BACKGROUND OF THE INVENTION

Topsheets used in absorbent articles, such as sanitary napkins, are required to have not only absorbing performance for smoothly transferring liquid body waste, e.g., menstrual blood or urine, to an underlying absorbent member but surface characteristics such that the surface thereof in contact with wearer's skin is soft enough not to cause skin irritation.

Currently available topsheets for absorbent articles include nonwoven fabrics made by various processes, perforated nonwoven fabrics, and perforated films of synthetic resins such as polyethylene, but none of them sufficiently satisfies the above-mentioned requirements of absorbing performance and surface characteristics.

Absorbent articles having a topsheet made of nonwoven fabric are disadvantageous in that waste liquid, e.g., menstrual blood or urine, discharged on the topsheet remains in the vicinity of the surface of the topsheet and gives discomfort or an unsanitary impression to a user on account of its color. Absorbent articles having a topsheet made of a perforated film relatively hide the color of blood or urine but are inferior in surface softness to those having a nonwoven fabric topsheet.

Japanese Patent 3131557 discloses wrinkled nonwoven fabric with a great number of streaky wrinkles (ridges) arrayed on its surface, which is used as a topsheet of an absorbent article. However, because of large empty spaces inside the ridges, liquid discharged on the topsheet penetrates into the surface of the wrinkles to make its color noticeable. Besides, this structure is not one that allows the liquid to quickly migrate to the absorbent member, which tends to cause overhydration.

Japanese Patent 3181195 discloses nonwoven fabric suitable for use as a female member of a mechanical fastener of disposable diapers, etc., which is obtained by partly joining a first fiber layer and a second fiber layer by heat fusion and thermally shrinking one of the first and second layers to make the other protrude toward one side to form regularly arrayed bulges. Because the two layers are partly joined by heat embossing in a very fine pattern, the nonwoven fabric is too hard for use as a topsheet of an absorbent article. Further, the fiber layer forming the bulges easily fuzzes up because of weak fusion bonds among constituent fibers. Therefore, if used as the topsheet of the absorbent article, the nonwoven fabric excessively irritates the skin to cause skin troubles.

JP-A-10-80445 discloses a topsheet for absorbent articles which comprises two nonwoven fabric layers and has a large number of openings, the two nonwoven fabric layers being joined together at the periphery of the individual openings. The topsheet disclosed may not be necessarily seen as sufficiently infiltratable for transferring liquid from the first layer (on the wearer's side) to the second layer (on the absorbent member side).

SUMMARY OF THE INVENTION

An object of the present invention is to provide a topsheet for absorbent articles which exhibits sufficient absorbing performance for making discharged body liquid such as blood or urine quickly migrate to the absorbent member and has excellent softness on its side to be brought into contact with wearer's skin for causing little skin irritation, preventing an itch, a rash or discomfort due to overhydration or irritation, and giving a wearer comfort.

Another object of the present invention is to provide an absorbent article which hides the color of a body liquid such as blood or urine discharged on the topsheet thereof and thereby gives a sanitary impression to a user and has excellent softness on the wearer's side to prevent an itch, a rash or discomfort due to physical irritation, and assures a wearer an excellent comfort (a cushioning feel) while being worn.

The first object of the present invention is accomplished by a topsheet for an absorbent article comprising a first layer disposed on the side of a wearer and a second layer disposed on the side of an absorbent member, the first layer and the second layer being partly joined together, and having protrusions and depressions on the side of a wearer, wherein the first and the second layers each comprise a fiber aggregate, the first layer has fusion-bonded fiber intersections, the first layer has an apparent thickness (t1) of 0.1 to 5 mm, the second layer has an apparent thickness (t2) of 0.2 to 3 mm, the apparent thickness ratio of the first layer to the second layer (t1/t2) is 0.5 to 8, the first layer has a fiber density (d1) of 0.001 to 0.05 g/cm$^3$, the second layer has a fiber density (d2) of 0.03 to 0.2 g/cm$^3$, and the fiber density (d2) of the second layer is higher than that (d1) of the first layer.

The second object of the present invention is accomplished by an absorbent article comprising a liquid permeable topsheet, a liquid impermeable backsheet, and a liquid retentive absorbent member interposed between the topsheet and the backsheet, wherein the topsheet comprises a first layer disposed on the side of a wearer and a second layer disposed on the side of an absorbent member and has protrusions and depressions on the side of a wearer, the first layer comprises a fiber aggregate having fusion-bonded fiber intersections, the first layer has an apparent thickness (t1) of 0.1 to 5 mm, the second layer has an apparent thickness (t2) of 0.2 to 3 mm, the apparent thickness ratio of the first layer to the second layer (t1/t2) is 0.5 to 8, the topsheet shows a through-thickness deformation of 0.03 to 0.3 mm per gf/cm$^2$ when compressed under a load of 10 gf/cm$^2$, and the topsheet has a surface whiteness (L value) of 60 or higher and a red plate hiding ratio of 40% or higher.

BRIEF DESCRIPTION OF THE DRAWINGS

The present invention will be more particularly described with reference to the accompanying drawings, in which.

DETAILED DESCRIPTION OF THE PREFERRED EMBODIMENTS

The present invention will be described in greater detail with reference to its preferred embodiments.

Figure 1:
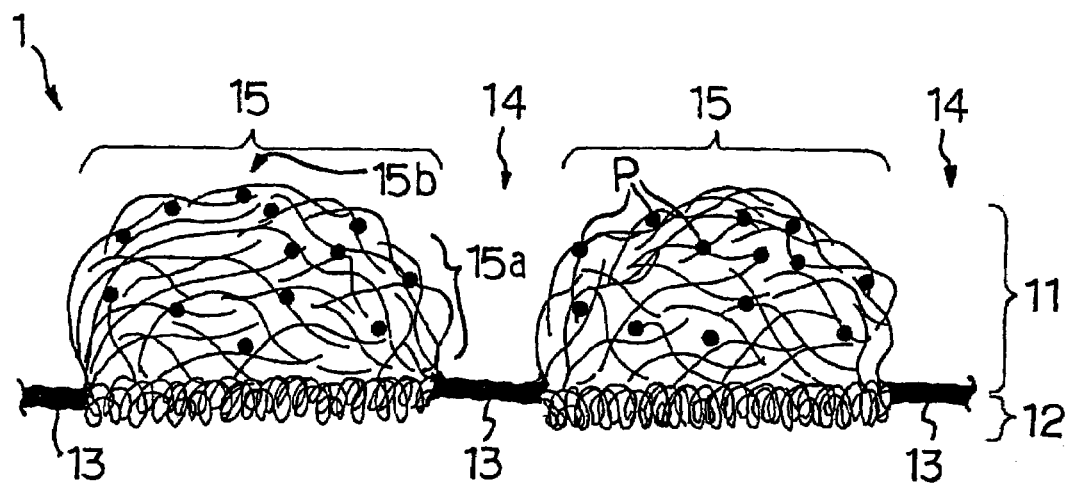
FIG. 1 is an exaggerated cross-sectional view of a topsheet according to the present invention, designed for use in a sanitary napkin.
Figure 3:
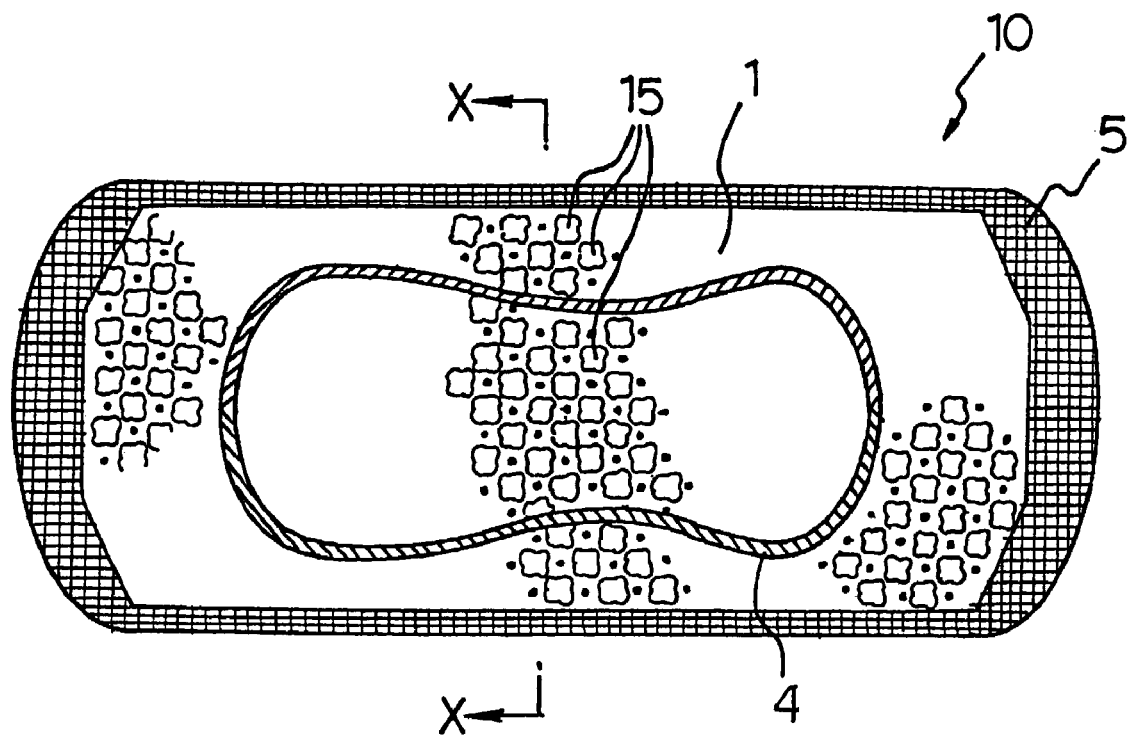
FIG. 3 is a plan of a sanitary napkin as an embodiment of the absorbent article according to the present invention, in which the topsheet of FIG. 1 is used.

An embodiment of the topsheet according to the present invention is described first. As shown in FIG. 3, a topsheet 1 according to this embodiment is used on the side of an absorbent article which is to come into contact with a wearer's skin. As shown in FIG. 1, the topsheet 1 comprises a first layer 11 disposed on the side of a wearer and a second layer 12 disposed on the side of the absorbent member.

The first layer 11 and the second layer 12 are each made of a fiber aggregate and are joined together in parts.

As shown in FIG. 1, the joints 13 of the first layer 11 and the second layer 12 are densified by compression to have an extremely smaller thickness than the other part of the topsheet 1. A large number of protrusions 15 are formed on the wearer's side of the topsheet 1 in a prescribed pattern, making a large number of depressions 14 on the joints 13. These protrusions 15 and the depressions 14 provide an uneven profile on the wearer's side of the topsheet 1.

The fiber aggregate forming the first layer 11 is nonwoven fabric having fusion-bonded fiber intersections P. The nonwoven fabric having fusion bonded fiber intersections P may also contain fibers that are not fusion bonded to other fibers. The fiber aggregate forming the second layer 12 may be either nonwoven fabric having fusion bonded fiber intersections or nonwoven fabric with no fusion bonded fiber intersections.

Because the first layer 11 is made of nonwoven fabric having fusion bonded fiber intersections P, the surface of the protrusions 15, which comes into contact with wearer's skin, suffers little fuzz that is liable to occur on nonwovens or fiber webs with no fusion bonded intersections. As a result, the topsheet 1 exhibits sufficient surface strength not to fuzz up while worn on friction with a wearer's body, giving little physical irritation to the skin and always assuring comfort for a wearer.

The first layer 11 has an apparent thickness (t1) of 0.1 to 5 mm, preferably 0.1 to 3 mm, still preferably 0.5 to 2.0 mm. The second layer 12 has an apparent thickness (t2) of 0.2 to 3 mm, preferably 0.3 to 3 mm, still preferably 0.5 to 2.0 mm. The apparent thickness ratio of the first layer to the second layer, t1/t2, is 0.5 to 8, preferably 1 to 5, still preferably 1 to 3.

With an apparent thickness t1 less than 0.1 mm, the part capable of being deformed under wearing pressure applied is insufficient, resulting in a failure to give a fluffy and soft feel. With t1 exceeding 5 mm, the liquid entering the protrusions must travel the increased distance to reach the second layer 12. As a result, the liquid is not smoothly absorbed under low pressure applied to spoil the surface clean impression (whiteness) aimed by the present invention.

With an apparent thickness t2 smaller than 0.2 mm, the second layer 12 will have a non-uniform fiber distribution. The present invention is characterized by a fiber density difference between the first and the second layers, and the capillary force produced by such a fiber density difference is made use of to develop such absorptivity that does not allow liquid to remain on the surface. If there is a non-uniform fiber distribution, it would be difficult to make a sufficiently dense structure, resulting in deviation from the objects of the invention. If the apparent thickness t2 is greater than 3 mm, the relatively dense structure of the second layer hinders liquid migration to the absorbent member, and the second layer retains an increased amount of liquid. This will reduce the hiding properties and the resistance to back flow of liquid.

If the apparent thickness ratio t1/t2 is smaller than 0.5, the proportion of the second layer's thickness in the total thickness of the topsheet is too large, which will lead to insufficient hiding properties and insufficient prevention of liquid back flow. If it exceeds 8, the proportion of the first layer's thickness in the total thickness of the topsheet is too large to make liquid smoothly migrate to the second layer which is denser and has a capillary force. It can follow that liquid remains on the surface to give a wearer discomfort.

Figure 5A:
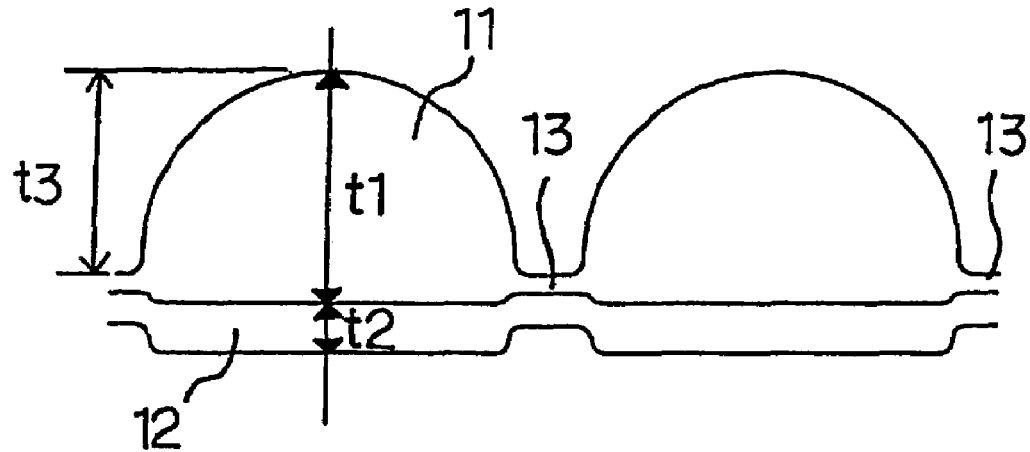
FIG. 5A and FIG. 5B each schematically illustrate the method of measurement in the present invention.

The height t3 (see FIG. 5A) of the protrusions is preferably 0.5 to 5 mm, still preferably 0.5 to 3 mm, taking wearing comfort and absorptivity into consideration. A height t3 smaller than 0.5 mm results in an increase in contact area with the skin, and some users may suffer from overhydration or a rash as a result. A height t3 larger than 5 mm is an increased distance the absorbed liquid must migrate to the second layer 12, and the liquid may fail to be absorbed smoothly under low pressure applied.

The apparent thickness of the first and the second layers can be measured as follows. A 30 mm-side square cut out of a topsheet is cut along a line substantially parallel with the longitudinal direction, namely, the fiber orientation direction (the machine direction) of the nonwoven fabric making the first layer, and passing through the joints 13. A magnified photograph is taken of the cut area under a microscope SZH10 supplied by Olympus Optical Co., Ltd. The real maximum thickness of the first layer, calculated from the magnification, is taken as the apparent thickness t1 of the first layer. The thickness of the second layer at the same position of measuring the first layer thickness is taken as the apparent thickness t2 of the second layer. In other words, the thicknesses of the first and the second layers are measured on the same straight line extending in the sheet thickness direction (see FIG. 5A). The protrusion height t3 is the height of from the bottom of a depression to the apex of a protrusion as measured in the same manner as for thicknesses t1 and t2.

In the topsheet 1, the second layer 12 has a higher fiber density than the first layer 11. The fiber density d1 of the first layer 11 is 0.001 to 0.05 g/cm$^3$, preferably 0.01 to 0.03/cm$^3$, and the fiber density d2 of the second layer 12 is 0.03 to 0.2 g/cm$^3$, preferably 0.04 to 0.1 g/cm$^3$.

Where the fiber densities d1 and d2 fulfill the above-described requirements, liquid discharged on the topsheet 1 swiftly enters the first layer, and the liquid in the first layer 11 then smoothly migrates to the second layer 12 by virtue of the fiber density difference. As a result, overhydration, skin troubles such as an itch and a rash, and discomfort which might occur due to liquid remaining on the surface of the topsheet can be prevented.

The first layer 11 and the second layer 12 are superposed on each other and joined in parts. They are in contact with each other in not only the joint areas 13 but other parts where the first layer 11 forms protrusions. It is desirable that the first layer 11 and the second layer 12 are in contact with each other with no gap over the entire area of each of the parts where the first layer 11 forms a protrusion.

If the fiber density dl is less than 0.001 g/cm$^3$, the first layer is so sparse that the topsheet 1 lacks hiding properties (inclusive of whiteness). Moreover, the first layer 11 has a decreased number of fusion bonded fiber intersections and is liable to fuzzing, which can impair the wearing comfort. With a d1 more than 0.05 g/cm$^3$, it is difficult to make an effective density difference from the second layer enough to produce a sufficient capillary force.

If the fiber density d2 of the second layer is smaller than 0.03 g/cm$^3$, the second layer fails to have such a dense structure as to develop a sufficient capillary force. As a result, liquid remains on the surface, and the topsheet has reduced hiding properties (low cleanliness feel). The second layer with a density d2 exceeding 0.2 g/cm$^3$ is too dense for securing smooth absorption, causing the liquid remaining problem.

For making the sparse-dense structure of the first and second layers to develop a sufficient capillary force, the ratio of the fiber density d2 to the fiber density d1, d2/d1, is preferably 1.2 or higher, still preferably 3 to 10.

The fiber densities of the first layer 11 and the second layer 12 are measured as follows. A 30 mm-side square cut out of a topsheet sample is cut along a line substantially parallel with the fiber orientation direction of the first layer, namely, the machine direction of the nonwoven fabric making the first layer, and passing through the joints 13. The apparent thickness t1 (mm) of the first layer is measured in the manner described supra.

Figure 5B:
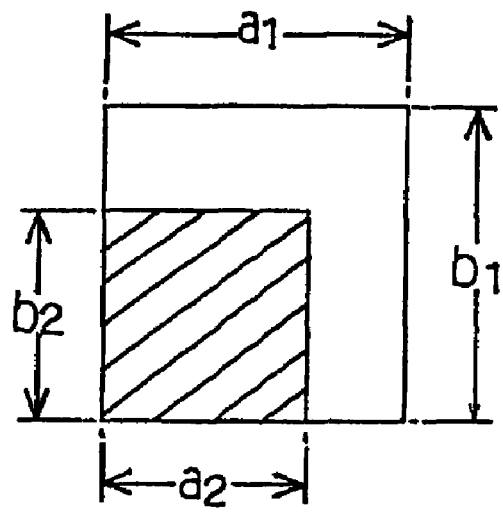

The percent area shrinkage (A; %) of the sample is calculated from the area of the first layer measured prior to shrinkage (before joining of the first layer and the second layer), represented by $a_1 \times b_1$, and the area of the first layer measured after shrinkage, represented by $a_2 \times b_2$, according to equation: $A=[(a_1 \times b_1 - a_2 \times b_2)/(a_1 \times b_1)] \times 100$ (see FIG. 5B). The basis weight P2 (g/m$^2$) of the first layer is calculated from the area shrinkage A (%) and the basis weight P1 (g/m$^2$) of the first layer before shrinkage (before joining of the first and the second layers) according to equation: $P2=P1 \times 100/(100-A)$. The fiber density d1 (g/cm$^3$) of the first layer is obtained from equation: $d1=P2 \times (1/1000) \times (1/t1)$.

The fiber density d2 of the second layer 12 is obtained in the same manner as for the d1. In the calculations, the apparent thickness t2 of the second layer 12 is obtained in the same manner as for the t1.

To make the sparse-dense structure of the first and the second layers, it is preferred that the capillary rise h2 according to the Klemm method of the second layer 12 be higher than that (h1) of the first layer 11, i.e., h2>h1 and more preferred that the h2 to h1 ratio (h2/h1) be from 1.2 to 5. A capillary rise according to the Klemm method will hereinafter be referred to as a Klemm's capillary rise.

As a method for producing the difference between the first and second layers in Klemm's capillary rise, it is preferred to make the fiber density different between the two layers (i.e., the second layer has a higher fiber density than the first layer), so that the second layer may exert a stronger capillary force than the first layer.

Other than the above method, it is effective to make hydrophilicity different between the two layers such that the second layer can have an increased Klemm's capillary rise by using a hydrophilizing agent having relatively higher hydrophilicity in the second layer. It is an effective manipulation, as a matter of course, to combine making a fiber density difference and making a hydrophilicity difference.

The Klemm's capillary rises of the first layer 11 and the second layer 12 are measured in accordance with JIS P8141 as follows. Measurement is carried out in the atmosphere satisfying the conditions specified in JIS P8111 (20° C., 65% RH). A 15 mm wide and 120 mm long strip cut out of a topsheet sample is rapidly vertically soaked up to 5 mm from its lower end in distilled water at 15 to 20° C. and allowed to stand for 10 minutes. The height (mm) of water having risen by capillary was read at the middle of the width.

Klemm's capillary rise is usually represented by an average of readings in the machine direction and an average of readings in the transverse direction of a sample. In the present invention, however, since the sample under test is nonwoven, the capillary rise is measured only in the longitudinal direction (generally the machine direction of the nonwoven) taking the fiber orientation direction into consideration, and an average of a plurality of specimens is obtained.

Figure 2:
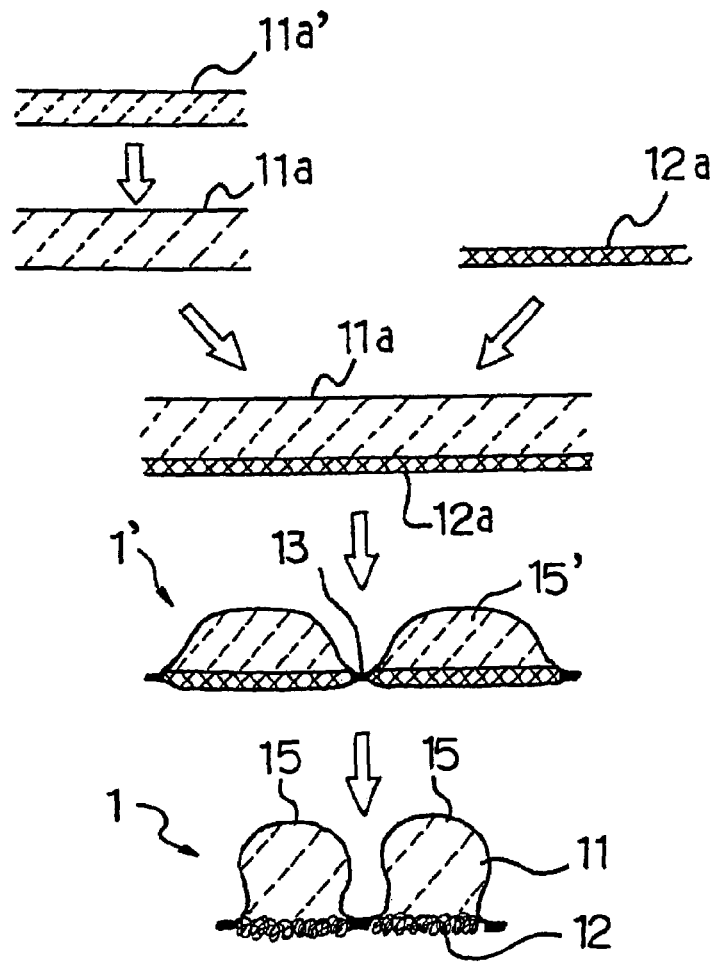
FIG. 2 shows the steps involved in the production of the topsheet shown in FIG. 1.

The process of producing the topsheet of the present invention will be described with particular reference to the topsheet 1. FIG. 2 is referred to.

In this particular embodiment, a nonwoven fabric 11a' having fusion bonded fiber intersections is treated with hot air into a bulky nonwoven fabric 11a having an apparent density of 0.004 to 0.05 g/cm$^3$ and a thickness of 0.3 to 5 mm.

The nonwoven fabric 11a' is not particularly limited as long as it has fusion bonded fiber intersections. On being subjected to the hot air treatment, the nonwoven fabric 11a' becomes the bulky nonwoven fabric as a first layer-forming material 11a. Such a first layer-forming material 11a provides a first layer 11 which is resistant to fuzzing.

The nonwoven fabric 11a' is preferably made up of fibers comprising thermoplastic polymers. Useful thermoplastic polymers include polyolefins, such as polyethylene and polypropylene; polyesters, such as polyethylene terephthalate; and polyamides. Conjugate fibers composed of these thermoplastic polymers, such as core-sheath conjugate fiber and side-by-side conjugate fiber, are also useful. It is preferred that the nonwoven fabric 11a' have substantially no thermal shrinkability or have no thermal shrinkability at temperatures causing a second layer-forming material described infra to initiate shrinking.

Thermoplastic polymer fibers having been treated with an appropriate hydrophilizing agent are preferably used to give a first layer 11 that is wettable with blood and capable of drawing blood from the surface. Water-absorbing fibers (fibers capable of absorbing water by themselves) such as cotton, rayon, and hydrophilized acrylic fiber may be used in place of, or in addition to, the fiber treated with a hydrophilizing agent. A difference of hydrophilicity between first and second layers can be produced by selecting the hydrophilicity or the coating amount of the hydrophilizing agent or by adjusting the amount of the water-absorbing fiber to be incorporated.

The nonwoven fabric 11a' includes thermal bond nonwoven, airlaid nonwoven, air-through nonwoven, and meltblown nonwoven.

The hot air treatment is carried out by, for example, (1) applying hot air to the surface of the nonwoven fabric 11a' or (2) forcing hot air through the thickness of the nonwoven fabric 11a'. The method (2) is preferred for sufficient recovery of thickness by heat.

Where the bulky nonwoven fabric 11a obtained by the hot air treatment has an apparent density less than 0.004 g/cm$^3$, the first layer 11 has an insufficient surface strength, and the protrusions 15 are liable to fuzz, which can impair the comfort for a wearer. If the apparent density is higher than 0.05 g/cm$^3$, the protrusions 15 tends to have insufficient sparseness for developing desired absorbing performance.

Where the bulky nonwoven fabric 11a is thinner than 0.3 mm, gaps tend to be formed between the first layer and the second layer on shrinking the second layer. If gaps are formed, liquid will be hindered from migrating from the first to second layers and may remain on the surface of the topsheet. With thicknesses greater than 5 mm, the proportion of the first layer's thickness in the total thickness of the top sheet becomes too large on shrinking the second layer only to make it difficult for liquid to migrate from the first to second layers. It follows that the topsheet fails to exhibit hiding properties and a dry feel.

The bulky nonwoven fabric 11a is superposed on a fiber aggregate 12a (a second layer-forming material), and the two layers are joined in a prescribed pattern. Any joining method that forms joints 13 where at least the bulky nonwoven fabric 11a has a smaller thickness than in other area is applicable. Thermal embossing or ultrasonic embossing is a recommended technique.

The pattern of the joints 13 includes spots, straight lines, curved lines (including continuous waves), lattices, and zigzags. The spots may have arbitrary shapes, such as circles (dots), triangles, and rectangles.

On partly joining the bulky nonwoven fabric 11a and the fiber aggregate 12a in a prescribed pattern, there is formed a composite sheet 1' consisting of the bulky nonwoven fabric 11a and the fiber aggregate 12a and having depressions on the joints 13 and low protrusions 15' made of the bulky nonwoven fabric 11a on the other parts.

Where the first layer-forming material and the second layer-forming material are partially fusion-bonded by thermal or ultrasonic embossing with an embossing surface (the peripheral surface of an embossing roll, for example) having embossing pins, a preferred pin density is 1 to 15 pins/cm$^2$, particularly 3 to 10 pins/cm$^2$, for avoiding absorption hindrance and ensuring smooth liquid penetration. After thermal shrinkage of the second layer, the number of the fusion bond joints 13 per cm$^2$ is preferably 1 to 30, still preferably 5 to 20, particularly preferably 5 to 10.

The fiber aggregate 12a as the second layer-forming material is preferably one that is capable of horizontally shrinking on being subjected to a prescribed treatment. A fiber aggregate which contains fibers capable of shrinkage when subjected to a prescribed treatment is preferably used. From the standpoint of easy processing and easy control on shrinkage, a fiber aggregate comprising thermally self-crimping fibers or consisting essentially or solely of self-crimping fibers is particularly preferred.

Self-crimping fibers are such that can be handled similarly to ordinary fibers for nonwovens before heat application and, when heated at a given temperature, crimp themselves in a helical form. Self-crimping fibers include conjugate fibers consisting of two thermoplastic polymers having different shrinkage characteristics in an eccentric core-sheath configuration or a side-by-side configuration. Examples of self-crimping conjugate fibers are given in JP-A-9-296325 and Japanese Patent 2759331.

The fiber aggregate 12a as the second layer-forming material may contain fibers other than the fibers capable of shrinking when subjected to a prescribed treatment. For example, the fiber aggregate 12a may contain water-absorbing fibers, such as rayon, cotton, and hydrophilic acrylic fiber.

Forms of the fiber aggregate 12a as the second layer-forming material include carded webs, thermal bond nonwovens, water needled nonwovens, needle punched nonwovens, solvent bonded nonwovens, spunbond nonwovens, and meltblown nonwovens.

The fiber aggregate 12a of the composite sheet 1' is then made to shrink in the horizontal direction (perpendicular to the thickness direction) by, for example, causing the fibers capable of shrinking when subjected to a prescribed treatment to shrink. Upon the horizontal shrinkage of the fiber aggregate 12a, the interfiber distance in the upper portion of the protrusions 15' increases to reduce the apparent density in this portion. At the same time, the distance between adjacent joints 13 reduces, and the apparent density of the fiber aggregate 12a between the joints 13 increases. The fiber aggregate 12a is preferably shrunken to an area shrinkage of 15 to 80%. There is thus produced the topsheet 1 for absorbent articles.

Figure 4:
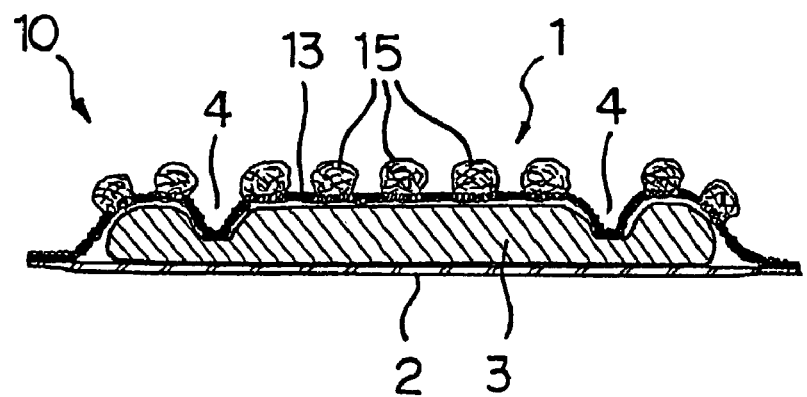
FIG. 4 is a cross-sectional view taken along X-X of FIG. 3.

A sanitary napkin as an embodiment of the absorbent article according to the present invention will then be described with reference to FIGS. 3 and 4. The sanitary napkin 10 comprises a liquid permeable topsheet 1, a liquid impermeable backsheet 2, and a liquid retentive absorbent member 3 disposed between the two sheets.

The topsheet 1 and the backsheet 2 are joined at their extensions from the periphery of the absorbent member 3 by known joining means, such as heat sealing and ultrasonic sealing, so that the absorbent member 3 is held between the two sheets 1 and 2. A leak preventive groove 4 surrounding the central portion (in the width and length) of the sanitary napkin 10 where blood is discharged is impressed from the topsheet 1 side.

The topsheet of the sanitary napkin 10 is the topsheet 1 of the above-described embodiment. The description about the topsheet 1 applies to the topsheet used in the sanitary napkin 10.

The topsheet 1 in the absorbent article 10 shows a through-thickness deformation of 0.03 to 0.3 mm/gf/cm$^2$, preferably 0.08 to 0.3 mm/gf/cm$^2$, when compressed under a load of 10 gf/cm$^2$. With the through-thickness deformation less than 0.03 mm, the topsheet is incapable of sufficient deformation under low pressure applied, failing to provide a wearer with fluffy and soft feel. A topsheet with the deformation more than 0.3 mm provides sufficient softness. However, such a topsheet cannot be obtained without increasing the thickness considerably, or such a fluffy topsheet allows its fibrous structure (interstices among fibers) to change so easily that a designed fibrous structure cannot be retained. Either case can result in significant impairment of the absorbing performance.

The through-thickness deformation per gf/cm$^2$ in compression under 10 gf/cm$^2$ is obtained as follows. Measurement is made with a compression tester KES-FB3, supplied by Katotec. The tester has a disk indenter having a compressing area of 2 cm$^2$. The disk indenter is vertically moved to give a compression-recovery load to such a sample as fabric or film to obtain a compression load-compressive deformation hysteresis loop for the compression-recovery cycle, which furnishes compression data, such as the sample thickness, the compression work done, the recovery properties, and the like.

More concretely, a 2.5 cm-side square specimen is cut out of the topsheet of an absorbent article 10 and set on KES-FB3. The disk indenter is moved down at a speed of 0.02 mm/sec to apply a compression load up to 50 gf/cm$^2$, at which the manual return switch is pushed to switch the downward movement to upward movement. The disk indenter is lifted until the load decreases to zero. A hysteresis loop for the compression-recovery cycle is plotted, from which the thickness t4 under a 10 gf/m$^2$ load in the process of compression is obtained. The thickness under a 0.5 gf/cm$^2$ load being taken as an initial thickness (t5), a thickness reduction (t5−t4)(mm) is calculated, from which a thickness deformation per gf/cm$^2$ is calculated. The specimen to be measured is cut out of an appropriate region of the topsheet 1 so as to have protrusions 15 all over the surface (the region containing the leak preventive groove 4 or the peripheral seal should be avoided if possible) or to have no or few collapsed protrusions 15. The specimen is preferably cut out of the region surrounded by the leak preventive groove 4, particularly the middle region of the width and the length of the absorbent article 10.

The topsheet 1 alone used in the absorbent article 10 has a surface whiteness L1 (described later) of 60 or higher, preferably 70 or higher, and a red plate hiding ratio (described later) of 40% or higher, preferably 45% or higher.

The difference between the surface whiteness La of the absorbent article (inclusive of the topsheet) before liquid absorption and the surface whiteness Lb of the absorbent article (inclusive of the topsheet) after absorbing 6 g of simulated blood, i.e., La-Lb, is preferably 40 or smaller, and the Lb is preferably 60 or higher, still preferably 65 or higher.

The topsheet 1 which has an L value (L1) of 60 or higher is equal to conventional film type topsheets in color hiding performance and capability of providing a clean impression (invisibility of the color of liquid absorbed). The L value represents the capabilities of covering blood having been absorbed and spread in the absorbent member. The closer the L value to 100, the whiter the sheet looks.

The absorbent article which has an Lb value of 60 or higher is equal to conventional absorbent articles having a film type topsheet in capabilities of providing a clean impression. The Lb value represents invisibility of the blood stains of the topsheet in the central portion of the absorbent article. The higher the Lb value, the less the amount of the liquid remaining on the surface of the topsheet.

La-Lb differences of 40 or larger mean that blood remains in the skin layer of the topsheet and looks outstanding. A smaller difference between La (L value of the absorbent article before absorption) and Lb (L value of the absorbent article after absorption) means a smaller amount of liquid remaining in the skin layer, a cleaner impression, and smaller possibility of causing overhydration and a skin rash.

The L value of the topsheet (L1), the red plate hiding ratio of the topsheet, and the L values of the absorbent article (inclusive of the topsheet) before absorption (La) and after absorption (Lb) are measured as follows.

Measurement of L Value of Topsheet (L1):

A color difference meter SZ-Σ80 supplied by Nippon Denshoku Industries, Co., Ltd. is used after calibration with a white reference plate. A light emitting pipe of 30 mm in diameter and a sample mount of 30 mm in diameter are chosen. A specimen of the topsheet is put on the glass mount with its side to be measured (the side coming into contact with a wearer) facing the light source. A specimen holder (black plate) attached to the instrument is placed on the specimen (opposite to the side to be measured). Five specimens cut out of different parts of a sample are measured, and the readings are averaged to yield the L value (surface whiteness) of the sample.

Measurement of Red Plate Hiding Ratio:

Measurements are taken in the same manner as for the L value, except for replacing the black specimen holder with the red plate attached to the instrument. First of all, the red side of the red plate (with no specimen) is measured to prepare a spectral curve, and the reflectance Ra at a selected wavenumber of 500 $cm^{-1}$ is recorded. Then, a specimen is placed between the glass and the red plate with the side to be measured facing the light source. Five specimens cut out of different parts of a sample are measured to obtain an average reflectance Rb at 500 $cm^{-1}$. A red plate hiding ratio is calculated from equation:

Red plate hiding ratio (%)=$[(Rb-Ra)/(100-Ra)] \times 100$

Measurement of Surface Whiteness (La) of Absorbent Article Before Absorption:

The surface whiteness of an absorbent article before absorption (La) is measured in the same manner as for the topsheet, except that the absorbent article (product) is placed on the glass mount with the topsheet side facing the light source.

Measurement of Surface Whiteness (Lb) of Absorbent Article After Absorption:

Simulated blood is prepared as follows. In a 2 liter beaker is put 1500 g of ion-exchanged water, and 5.3 g of sodium carboxymethyl cellulose (CMC-Na, available from Kanto Kagaku K.K.) is dissolved therein by stirring with a magnetic stirrer. Separately, 556 g of ion-exchanged water is put into a 1 liter beaker, and 27.0 g of sodium chloride and 12 g of sodium hydrogencarbonate ($NaHCO_2$, available from Kanto Kagaku K.K.) are dissolved therein by stirring with a stirrer. The resulting two solutions and 900 g of glycerin are mixed up by stirring in a 3 liter beaker.

To the mixture are added 15 ml of aqueous solution of nonionic surfactant "Emulgen 935" (available from Kao Corp.) having a concentration of 1 g/L (surfactant/water) and 0.3 g of Red #2 (produced by Daiwa Kasei K.K. and available from Aisen K.K. and Hodogaya Chemical Co., Ltd.), followed by stirring. The mixture is filtered by suction through a glass filter to prepare simulated blood.

Simulated blood may also be prepared by using other nonionic surfactants than the aforementioned one to obtain the same results. However, the amount of surfactant should be adjusted such that the contact angle of the simulated blood falls within the range of 35-40° with respect to the surface of a glass plate. The contact angle is obtained by measuring a contact angle of simulated blood with respect to the glass surface (cleansed by ethanol) with use of a contact angle measuring apparatus (manufactured by KYOWA INTERFACE SCIENCE CO., LTD., FACE Contact Angle Meter CA-A type).

Six grams of the simulated blood put in a 10 ml beaker is carefully poured through a pouring tool on the topsheet side of an absorbent article the surface whiteness of which has been measured. The pouring tool consists of an acrylic plate (100 mm×200 mm×8 mm (t)) having a through-hole of 10 mm in diameter at the center thereof and a hollow cylinder made of a smaller-diametered cylinder of 10 mm in inner diameter and a larger-diametered cylinder of 22 mm in inner diameter concentrically connected in series via a joint tapered at an angle of 45° with the axis of the cylinders, the end of the smaller-diametered cylinder being concentrically joined to the through-hole of the acrylic plate. The pouring tool is placed on the absorbent article with its through-hole at the center of the length and width of the absorbent article. Simulated blood (6 g) is poured into the opening of the larger-diametered cylinder over about 5 seconds and discharged from the hole of the plate. After the pouring, the absorbent article is allowed to stand for 120 seconds, and the surface whiteness Lb is measured in the same manner as for the La value (L value before absorption).

The material of the backsheet 2 and the absorbent member 3 constituting the absorbent article 10 can be of any materials that have conventionally been employed in absorbent articles such as disposable diapers. For example, the absorbent member 3 can be made of a fiber aggregate and a superabsorbent polymer. The fiber aggregate includes nonwoven fabrics and fiber webs. The superabsorbent polymer is used as held, e.g., in the interstices of fibers of the fiber aggregate or between layers of a multilayer structure made of fiber aggregates.

The present invention is not limited to the above-described embodiments. For example, the topsheet which can be used in the absorbent article as claimed in the present invention is not limited to one that satisfies all the requirements of the topsheet as claimed in the present invention, and the topsheet for absorbent article as claimed in the present invention is not limited to one that satisfies all the requirements of the topsheet which can be used in the absorbent article as claimed in the present invention.

The absorbent articles according to the present invention include not only sanitary napkins described supra but other products having a liquid permeable topsheet, a liquid impermeable backsheet, and an absorbent member interposed therebetween which are adapted to absorb and retain liquid body waste such as urine and menstrual blood, such as incontinence pads, panty liners, and disposable diapers.

EXAMPLE 1

The present invention will now be illustrated in greater detail with reference to Examples. Unless otherwise noted, all the percents and ratios are by weight.

Preparation of Topsheet:

Thermally fusion bondable core-sheath conjugate fiber (2.2 dtex×51 mm) consisting of a polyethylene terephthalate core and a polyethylene sheath available from Daiwabo Co., Ltd. was carded into a web and heat treated at 120° C. to fusion bond the fiber intersections to prepare nonwoven fabric having a basis weight of 15 g/m$^2$. The nonwoven fabric was subjected to hot air treatment at 70° C. to obtain bulky nonwoven fabric (first layer-forming material) having a thickness of 1 mm and an apparent density of 0.025 g/cm$^3$.

Separately, helically self-crimping fiber CPP (2.2 dtex×51 mm, available from Daiwabo Co., Ltd.) was carded into a web having a basis weight of 35 g/m$^2$ (second layer-forming material).

The first layer-forming material and the second layer-forming material were superposed on each other and partly joined together by ultrasonic embossing using an embossing plate having standing pins in a dot pattern. The dot pattern of the standing pins is repetition (except for the edges of the embossing roll) of a unit pattern consisting of a central pin C, a pair of pins arranged on a straight line parallel to the longitudinal direction (MD) and passing through the center of the pin C at a center-to-center distance of about 7 mm from the pin C, a pair of pins arranged on a straight line parallel to the width direction (CD) and passing through the center of the pin C at a center-to-center distance of about 7 mm from the pin C, and two pairs of pins each arranged on a straight line passing through the center of the pin C and making an angle of 45° with the MD and the CD at a center-to-center distance of about 5 mm from the pin C.

The resulting composite sheet was heated at 130° C. for about 1 to 10 minutes to is shrink the second layer-forming material in the horizontal direction to an area shrinkage of 56% to obtain a topsheet having a large number of protrusions 15 as shown in FIG. 1.

The resulting topsheet was examined to reveal that the fibers constituting the side wall 15a of each protrusion 15 and nearby fibers were oriented almost in parallel with each other along the curved plane between the apex 15b and the joint 13. The resulting topsheet was examined for apparent thickness t1 of the first layer, apparent thickness t2 of the second layer, fiber density d1 of the first layer, fiber density d2 of the second layer, Klemm's capillary rise h1 of the first layer, Klemm's capillary rise h2 of the second layer, and through-thickness deformation per gf/cm$^2$ in compression under a 10 gf/cm$^2$ load. The results obtained are shown in Table 1 below.

Production of Absorbent Article:

The topsheet prepared above and a polyethylene film backsheet (one used in Lorie UN-f-11 Sarasara Cushion Slim with no wings, available from Kao Corp.) were set on the upper and the lower sides, respectively, of an absorbent member (thickness: 4.5 mm; an aggregate made of 200 g/m$^2$ of fluff pulp and 40 g/m$^2$ of absorbent polymer (acrylic acid-sodium acrylate copolymer) and wrapped in absorbent paper having a basis weight of 16 g/m$^2$). A leak preventive groove 4 and peripheral seal 5 were formed to make a sanitary napkin shown in FIGS. 3 and 4.

Surface whitenesses L1 of the topsheet alone, La of the absorbent article before absorption, and Lb of the absorbent article after absorption were measured. The results are shown in Table 1.

EXAMPLE 2

A topsheet was prepared in the same manner as in Example 1, except that a bulky nonwoven fabric having a thickness of 0.9 mm, an apparent density of 0.013 g/cm$^3$, and a basis weight of 12 g/m$^2$ was prepared as a first layer-forming material and that the second layer-forming web partly joined with the bulky nonwoven fabric was shrunken at an area shrinkage of 30%.

EXAMPLE 3

A topsheet was prepared in the same manner as in Example 2, except that the percent area shrinkage was changed to 15%.

EXAMPLE 4

Helically self-crimping fiber CPP (2.2 dtex×51 mm, available from Daiwabo Co., Ltd.) and thermally fusion bondable core-sheath conjugate fiber (2.2 dtex×51 mm) consisting of a polyethylene terephthalate core and a polyethylene sheath available from Daiwabo Co., Ltd. were mixed at a weight ratio of 50:50 and carded into a web having a basis weight of 35 g/m$^2$.

A topsheet was prepared in the same manner as in Example 1, except for using the resulting web as a second layer-forming material.

COMPARATIVE EXAMPLE 1

A topsheet was prepared in the same manner as in Example 1, except for using, as a first layer-forming material, a web having a basis weight of 15 g/m$^2$ prepared by carding the same fiber as used in Example 1 (having no fusion-bonded fiber intersections).

COMPARATIVE EXAMPLE 2

A topsheet was prepared in the same manner as in Example 1, except for using, as a first layer-forming material, spunbond nonwoven fabric made solely of polypropylene fiber and having a basis weight of 12 g/m$^2$.

COMPARATIVE EXAMPLE 3

The topsheet used in Lorie UN-f-11 Sarasara Cushion Slim (with no wings), available from Kao Corp., was examined.

COMPARATIVE EXAMPLE 4

The topsheet used in Lorie DR-h-114 Dry-up Mesh Regular, available from Kao Corp., was examined.

The topsheet of Comparative Example 3 is made of perforated nonwoven fabric of core-sheath conjugate fiber consisting of a polyethylene telephthalate core and a polyethylene sheath and the nonwoven fabric is provided with 10 to 15 pores/cm$^2$ of about 0.8 to 1 mm in diameter. The topsheet of Comparative Example 4 is made of perforated polyethylene film.

Evaluation of Absorbing Performance (Blood Hiding Properties):

Sanitary napkins were produced under equal conditions with the same materials, except for using each of the topsheets prepared in Examples 1 to 4 and Comparative Examples 1, 2 and 4. Twelve females were asked to actually use the sanitary napkins and compare them with reference sanitary napkins Lorie UN-f-11 Sarasara Cushion Slim (with no wings) for blood hiding properties. Ten persons out of the twelve judged that the topsheet of Example 1 made blood more obscure than that of the reference article (supported the product of the present invention).

Evaluation of Comfort in Use:

The 12 females were also asked to evaluate the soft feel of the topsheet while worn in the same actual testing. Five out of twelve judged that the topsheet of Example 1 was softer than that of the reference article, and the rest judged these topsheets equal in softness.

Organoleptic Test on Fuzz:

Twenty females evaluated the topsheets of Examples 1 to 4 and Comparative Examples 1 to 4 by appearance and feel to the touch. As a result, 16 out of 20 (80%) judged the topsheet of Comparative Example 1 no good because of fuzz, and all judged that fuzz, if any, of the other topsheets was not such to care about.

It is seen from the results of evaluation in Examples and Comparative Examples that the topsheet according to the present invention is excellent in both absorbing performance and surface softness. That is, the topsheet of the invention makes liquid waste such as menstrual blood or urine quickly migrate to the absorbent member and feels soft (cushioning and fluffy) on the side in contact with a wearer, giving little irritation to the skin. In particular, protrusions of the topsheet the first layer of which is made of nonwoven fabric having fusion bonded fiber intersections have a reduced fiber density and improved resistance against fuzzing.

It has also been proved that the absorbent article according to the present invention gives a user a clean impression because of the topsheet's capability of making the color of discharged liquid waste such as menstrual blood or urine obscure, has excellent softness on the wearer's side to prevent an itch, a rash or discomfort due to physical irritation, and assures a wearer an excellent comfort while being worn.

The topsheet for an absorbent article according to the present invention has not only absorbing performance for smoothly transferring liquid body waste, e.g., menstrual blood or urine, to an underlying absorbent member but surface characteristics such that the surface thereof in contact with wearer's skin is soft enough not to cause skin irritation. Therefore, it prevents an itch, a rash or discomfort due to overhydration or irritation and assures a wearer an excellent comfort (a cushioning feel) while being worn.

The absorbent article according to the present invention gives a user a clean impression because of the topsheet's capability of making the color of discharged liquid waste such as menstrual blood or urine obscure, has excellent softness on the wearer's side to prevent an itch, a rash or discomfort due to physical irritation, and assures a wearer an excellent comfort (a cushioning feel) while being worn.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

| | | Example | | | | Comparative Example | | | |
|---|---|---|---|---|---|---|---|---|---|
| | | 1 | 2 | 3 | 4 | 1 | 2 | 3 | 4 |
| Topsheet: | | | | | | | | | |
| Apparent Thickness (mm) | t1 | 2.00 | 1.40 | 0.60 | 1.50 | 2.30 | 0.15 | 0.42 | 0.57 |
| | t2 | 1.00 | 0.80 | 1.10 | 1.50 | 1.17 | 1.18 | — | — |
| | t1/t2 | 2.0 | 1.8 | 0.6 | 1.0 | 2.0 | 0.1 | — | — |
| Fiber Density (g/cm$^3$) | d1 | 0.017 | 0.012 | 0.024 | 0.020 | 0.014 | 0.080 | 0.060 | — |
| | d2 | 0.080 | 0.063 | 0.037 | 0.047 | 0.086 | 0.086 | — | — |
| | d2/d1 | 4.7 | 5.3 | 1.5 | 2.4 | 6.1 | 1.1 | — | — |
| Klemm's Capillary Rise (mm) | h1 | 6 | 6 | 6 | 6 | 4 | 6 | 6 | — |
| | h2 | 14 | 12 | 9 | 13 | 14 | 13 | — | — |
| Through-thickness Deformation at 10 gf/cm$^2$ (mm/gf/cm$^2$) | | 0.08 | 0.08 | 0.06 | 0.14 | 0.16 | 0.12 | 0.05 | 0.01 |
| Whiteness L1 | | 80 | 69 | 62 | 77 | 80 | 60 | 62 | 75 |
| Red Plate Hiding Ratio (%) | | 66 | 49 | 42 | 63 | 65 | 40 | 34 | 56 |
| Height t3 of Protrusion (mm) | | 2.60 | 2.00 | 1.30 | 2.70 | 3.00 | 1.85 | — | — |
| Absorbent Article: | | | | | | | | | |
| Surface Whiteness | La | 96 | 95 | 95 | 97 | 95 | 96 | 96 | 97 |
| | Lb | 74 | 70 | 65 | 76 | 74 | 54 | 60 | 74 |
| | La − Lb | 22 | 25 | 30 | 21 | 21 | 42 | 36 | 23 |
| Organoleptic Test on Fuzz (NG Ratio) (%) | | 0 | 0 | 0 | 0 | 80 | 0 | 0 | 0 |

This application claims the priority of Japanese Patent Application Nos. 2001-398779 filed Dec. 28, 2001 and 2002-301297 filed Oct. 16, 2002, which are incorporated herein by reference.

What is claimed is:

1. A topsheet for an absorbent article comprising:
a first layer disposed on the side of a wearer; and
a second layer disposed on the side of an absorbent member,
wherein the first layer and the second layer being partly joined together in densified joints, said densified joints being arranged in a spot pattern said spot pattern is in a checkerboard arrangement, and having protrusions and depressions on the side of a wearer, wherein said protrusions in the first layer are made by the formation of helically crimped fibers in the second layer and thermal shrinkage of the second layer, wherein the depressions contain the densified joints, wherein said first layer and said second layer each comprise a fiber aggregate, said first layer has fusion-bonded fiber intersections that are formed in the protrusions of the topsheet, and said second layer comprises said helically crimped fibers that include conjugate fibers consisting of two thermoplastic polymers have different shrinkage characteristics in an eccentric core-sheath configuration or side-by-side configuration, wherein said first layer has an apparent thickness (t1) of 0.1 to 5 mm, said second layer has an apparent thickness (t2) of 0.3 to 3 mm, the apparent thickness ratio of said first layer to said second layer (t1/t2) is 1 to 5, wherein said first layer has a fiber density (d1) of 0.001 to 0.05 g/cm$^3$, said second layer has a fiber density (d2) of 0.03 to 0.2 g/cm$^3$, and the fiber density (d2) of said second layer is higher than the fiber density (d1) of said first layer; and wherein said first layer and said second layer are in contact with each other in not only the joint areas but also other parts.

2. The topsheet according to claim 1, wherein the ratio of the fiber density d2 of said second layer to the fiber density d1 of said first layer, d2/d1, is 1.2 or higher.

3. The topsheet according to claim 1, wherein said second layer has a higher capillary rise according to the Klemm method than said first layer.

4. The topsheet according to claim 1, wherein the two thermoplastic polymers having different shrinkage characteristics in said second layer are in the eccentric core-sheath configuration.

5. The topsheet according to claim 1, wherein the two thermoplastic polymers having different shrinkage characteristics in said second layer are in the eccentric side-by-side configuration.

6. An absorbent article comprising the liquid permeable topsheet of claim 1, a liquid impermeable backsheet, and a liquid retentive absorbent member interposed between the topsheet and the backsheet, wherein:

said topsheet shows a through-thickness deformation of 0.03 to 0.3 mm per gf/cm$^2$ when compressed under a load of 10 gf/cm$^2$, and said topsheet has a surface whiteness of 60 or higher in terms of L value and a red plate hiding ratio of 40% or higher.

7. The absorbent article according to claim 6, wherein the difference between the surface whiteness La, in terms of L value, of the absorbent article before liquid absorption and the surface whiteness Lb, in terms of L value, of the absorbent article after absorbing 6 g of simulated blood, La–Lb, is 40 or smaller, and the Lb is 60 or higher.

* * * * *